(12) United States Patent
Jones et al.

(10) Patent No.: US 8,492,153 B2
(45) Date of Patent: Jul. 23, 2013

(54) METHOD FOR DETERMINING VOLUME OF ORGANIC MATTER IN RESERVOIR ROCK

(75) Inventors: Peter J. Jones, Dhahran (SA); Henry I. Halpern, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 12/449,209

(22) PCT Filed: Feb. 15, 2008

(86) PCT No.: PCT/US2008/002102
§ 371 (c)(1),
(2), (4) Date: Oct. 28, 2009

(87) PCT Pub. No.: WO2008/100614
PCT Pub. Date: Aug. 21, 2008

(65) Prior Publication Data
US 2010/0057409 A1    Mar. 4, 2010

Related U.S. Application Data

(60) Provisional application No. 60/902,149, filed on Feb. 16, 2007.

(51) Int. Cl.
*G01N 33/24* (2006.01)
(52) U.S. Cl.
USPC ............... 436/29; 436/25; 436/30; 436/31; 436/32; 436/183
(58) Field of Classification Search
USPC ........................... 436/25, 29–32, 183
See application file for complete search history.

(56) References Cited

U.S. PATENT DOCUMENTS

| | | | | |
|---|---|---|---|---|
| 3,622,525 A * | 11/1971 | Miller | ............... | 521/157 |
| 4,093,420 A * | 6/1978 | Grayson et al. | ............... | 356/30 |
| 4,106,908 A * | 8/1978 | Leplat-Gryspeerdt | ............... | 436/29 |
| 4,149,804 A * | 4/1979 | Chew, III | ............... | 356/416 |
| 4,229,181 A * | 10/1980 | Espitalie et al. | ............... | 436/31 |
| 4,352,673 A * | 10/1982 | Espitalie et al. | ............... | 436/145 |
| 4,419,214 A * | 12/1983 | Balint et al. | ............... | 208/402 |
| 4,532,024 A * | 7/1985 | Haschke et al. | ............... | 208/390 |

(Continued)

OTHER PUBLICATIONS

Halpern, H. I. et al, Abstract: Applications of Pyrolysis to Optimize Oil Field Development in Saudi Arabia: Part 1—Prior to Drilling Phase, AAPG Search and Discovery Article #90026 © 2004 AAPG Annual Meeting, Dallas, Texas, Apr. 18-21, 2004, one page.*

(Continued)

*Primary Examiner* — Arlen Soderquist
(74) *Attorney, Agent, or Firm* — Abelman, Frayne & Schwab

(57) ABSTRACT

A method for calculating the volume of various predetermined organic end-members in samples of rock at various depths in oil reservoir rock is utilized to produce one or more graphic displays that are use to interpret the data to identify, e.g., tar mats, in order to improve the efficient production of hydrocarbons from the well. Data is collected from the samples by known pyrolysis and compositional modeling methods; additional data is obtained by elemental analysis to determine weight percentages of C, H, N, S and O in the selected end-members and characterization of physical properties of representative samples of the reservoir rock, e.g., from core samples; the data is then processed in accordance with the method to provide a series of data points used to produce the graphic displays for visual interpretation.

14 Claims, 7 Drawing Sheets

U.S. PATENT DOCUMENTS

| | | | | |
|---|---|---|---|---|
| 4,578,356 A | * | 3/1986 | Larter | 436/31 |
| 4,609,821 A | * | 9/1986 | Summers | 250/255 |
| 4,798,805 A | * | 1/1989 | Issenmann | 436/157 |
| 5,174,966 A | * | 12/1992 | Durand et al. | 422/102 |
| 5,389,550 A | * | 2/1995 | Ishida et al. | 436/32 |
| 5,811,308 A | * | 9/1998 | Espitalie et al. | 436/145 |
| 5,843,787 A | * | 12/1998 | Trabelsi et al. | 436/139 |
| 5,866,814 A | * | 2/1999 | Jones et al. | 73/152.11 |
| 6,271,518 B1 | * | 8/2001 | Boehm et al. | 250/255 |
| 6,725,920 B2 | * | 4/2004 | Zhang et al. | 166/245 |
| 6,823,298 B1 | | 11/2004 | Jones et al. | |
| 7,344,889 B2 | * | 3/2008 | Kelemen et al. | 436/29 |
| 7,772,004 B2 | * | 8/2010 | Lorant | 436/32 |
| 2004/0019437 A1 | * | 1/2004 | Kelemen et al. | 702/27 |
| 2007/0162264 A1 | | 7/2007 | Jones et al. | |

OTHER PUBLICATIONS

Jones, P. J. et al, Abstract: Applications of Pyrolysis to Optimize Oil Field Development in Saudi Arabia: Part 2—"Real-Time" Application on Horizontal Wells, AAPG Search and Discovery Article #90026 © 2004 AAPG Annual Meeting, Dallas, Texas, Apr. 18-21, 2004, one page.*

Guillen, M. D. et al, Energy & Fuels 1991, 5, 188-192.*

Blanc, P. et al, Energy & Fuels 1992, 6, 666-677.*

Peters, K. E. et al, in The Petroleum System—from Source to Trap 1994, chapter 5, pp. 93-120, Magoon, L. B. et al, ed, AAPG Memior 60.*

Schwark, L. et al, Organic Geochemistry 1997, 26, 19-31.*

Pan, C. et al, Organic Geochemistry 2003, 34, 357-374.*

Pan, C. et al, Organic Geochemistry 2005, 36, 633-654.*

Orr, W. L., in Advances in Organic Geochemistry, Proceedings of the 10$^{th}$ International Meeting 1983 (meeting date 1981), 775-787, Bjoroey, M. editor, Wiley, Chichester, United Kingdom.*

Peters, K. E., AAPG Bulletin 1986, 70, 318-329.*

Carpentier et al., "Tar mats and residual oil distribution in a giant oil field offshore Abu Dhabi," Journal of Petroleum Science & Engineering, 58, 2007, pp. 472-490.

* cited by examiner

METHOD FOR DETERMINING VOLUME OF ORGANIC MATTER IN RESERVOIR ROCK

CROSS REFERENCE TO RELATED APPLICATIONS

This application is a national phase of PCT application No. PCT/US2008/002102, filed Feb. 15, 2008, which claims priority under 35 U.S.C. 119(e) to U.S. Provisional Application No. 60/902,149, filed Feb. 16, 2007.

FIELD OF THE INVENTION

This invention relates to the geochemical analysis of reservoir rock samples obtained from existing core samples or during drilling operations to characterize the organic matter in order to manage the drilling and production of hydrocarbons from the reservoir.

BACKGROUND OF THE INVENTION

The purpose of oil reservoir characterization is to provide a detailed description of the rock, pore space, and fluid system so that the behavior of the reservoir either under production or during water injection can be understood and modeled over the life of the reservoir. Pyrolysis methods that have been developed to assess reservoir characteristics are disclosed in U.S. Pat. Nos. 5,866,814 and 6,823,298, the disclosures of which are incorporated herein by reference. These methods are based on assessing the residual hydrocarbon staining that is found on samples from oil reservoirs obtained during either drilling or coring operations. When assessing movable hydrocarbons, (i.e., oil), the residual hydrocarbons that are analyzed represent only a fraction of those that are present in a bulk sample under reservoir conditions. These "moveable" hydrocarbons are lost during the drilling process via flushing with mud filtrate and through volatilization when the samples are brought from reservoir to atmospheric conditions. Nonetheless, the characteristics of the residual "moveable" hydrocarbons are well preserved and well understood in relation to reservoir performance and can be exploited successfully by the prior methods.

Residual hydrocarbons from "immoveable" hydrocarbons are present in rock samples in roughly the same proportional quantity in the reservoir. Some losses may occur during storage and exposure to air, but these losses are relatively minor. In an oil reservoir, the "immoveable" hydrocarbons of most concern are tar (solid material that is similar to the asphaltene component in crude oil and soluble in organic solvents) and pyrobitumen (insoluble tar, originally derived from tar). These two materials are the primary substances that lead to a reduction in the ability to move fluids (either oil or water) in a reservoir. Therefore, the ability to quantify these materials in terms of their volume, and in relation to reservoir porosity, provides a means to assess their effect on reservoir performance that has been difficult to attain through the prior art methods available to the industry.

For example, a frequently utilized method of assessing hydrocarbon saturation in a reservoir is via the Archie Equation, which utilizes reservoir parameters such as the cementation and saturation exponents in the calculation. These factors are sensitive to changes in lithology or facies within a reservoir. However, these parameters are also sensitive to the wettability of the reservoir, which typically changes drastically when encountering a zone with a substantial quantity of tar. Thus, the calculation of the hydrocarbon saturation in a reservoir is compromised if the composition of that material is variable. Furthermore, the Archie Equation does not discriminate between oil, tar and pyrobitumen.

Another means of assessing oil reservoir fluid properties are NMR logging tools. These tools provide very useful information regarding the nature of reservoir fluid, whether it is light oil, medium oil, heavy oil or tar. However, the available analytic apparatus and methods do not include a means for the explicit calculation of the volumes of these components, and, like all petrophysical logging tools, rely on interpretations based on indirect measurements and assumptions.

DEFINITIONS

The following definitions are provided for abbreviations and terms that are used in the further description of the invention.

API Gravity—is a specific gravity scale developed by the American Petroleum Institute (API) for measuring the relative density of various petroleum liquids. API gravity is graduated in degrees on a hydrometer instrument and was designed so that most values would fall between 10 and 70 API gravity degrees. The formula used to obtain the API gravity of petroleum liquids is the following:

$$\text{API gravity} = (141.5/SG \text{ at } 60° \text{ F.}) - 131.5,$$

where SG is the specific gravity of the material at 60° F.

Crucible—The stainless steel container in which the sample is pyrolyzed.

Density ($\rho$)—Mass per unit of volume. Density is typically reported in g/cm$^3$; however, the units of mg/µl are an equivalent expression and are more useful in converting results from pyrolysis.

Elemental Analysis—Elemental analysis is a process where a sample of some material (e.g., oil, tar, pyrobitumen, etc.) is analyzed for its elemental composition. Elemental analysis can be accomplished by a number of methods, including: mass spectrometric atomic spectroscopy, X-ray fluorescence, etc. In the assessment of hydrocarbons, such as oil, tar, and pyrobitumen, the elements that are of most concern (due to abundance) are: carbon, hydrogen, nitrogen, sulfur, and oxygen.

End-member (EM)—A consistent organic matter or hydrocarbon type that can be distinguished through pyrolytic analysis, and that includes oil, soluble tar, pyrobitumen (or insoluble tar), kerogen, coal, drilling mud contaminants and other materials that are associated with local conditions.

Flame Ionization Detector (FID)—The most commonly used detector for assessing the quantities of organic compounds. The response of an FID to hydrocarbons is proportional to the number of carbon atoms contained in hydrocarbon compounds, or compounds that contain hydrocarbon "units" within their structure.

Grain Density—The density of the grains in a formation or core sample. As used in log and core analysis, the term refers to all the solid material in the rock. The grain density of core samples is calculated from the measured dry weight divided by the grain volume. In logs, grain density is calculated from the density log, using an estimate of porosity and knowledge of the fluid content.

HC—Abbreviation for hydrocarbons, THC is used for Total Hydrocarbons. As used in this description when referring to hydrocarbons and total hydrocarbons, HC means compounds, or portions of compounds that have hydrocarbon units with the formula $C_nH_{xn}$, where n is the number of carbon atoms, and x is the average number of hydrogen atoms per carbon atom. The hydrocarbons referred to herein are determined on the basis of results obtained from use of a Flame Ionization Detector (FID). This value is to be distinguished from the quantification of hydrocarbons determined from chemical group type separations (SARA analysis) commonly performed in petroleum geochemistry and that yield only the saturated and aromatic fractions as "pure" hydrocarbons. Non-hydrocarbon fractions from SARA analysis include the resin and asphaltene fractions which contain abundant $C_nH_{xn}$ components and that register responses as "hydrocarbons" when subjected to FID analysis.

H/C Ratio—The atomic ratio of hydrogen to carbon in organic matter.

Hydrogen Index (HI)—The Hydrogen Index is a parameter that is employed to evaluate source rocks using the commercially available Rock-Eval™ pyrolysis instrument or other suitable commercial instruments such as the Humble Source Rock ("SR") Analyzer or the Geofina total hydrocarbon analyzer. The HI parameter measures the quantity of "pyrolyzable" hydrocarbons ($S_2$) present in a sample relative to the amount of total organic carbon (TOC). The equation is as follows: $HI = (S_2/TOC) \times 100$.

LV—Abbreviation for "light volatile" components that as used herein refers specifically to the weight in milligrams of HC released per gram of rock at the static temperature condition of 180° C. (195° C. on a Humble SR Analyzer) for 3 minutes when the crucible containing the rock sample is inserted into the pyrolytic chamber prior to the temperature-programmed pyrolysis of the sample.

POPI—The pyrolytic oil-productivity index method as disclosed in U.S. Pat. No. 5,866,814 and further applied in U.S. Pat. No. 6,823,298.

SARA—An analytical method in which results are reported in terms of Saturate, Aromatic, Resin and Asphatene fractions, of which only the first two are considered to be hydrocarbons, the latter being non-hydrocarbons, although still composed predominantly of H and C.

TD—Abbreviation for "thermally distillable" components that, as used herein, refers specifically to the weight in milligrams of HC released per gram of rock at a temperature between 180° C. (195° C. on a Humble SR Analyzer) and $T_{min}$(° C.).

TC—Abbreviation for "thermally crackable" components that as used herein refers specifically to the weight in milligrams of HC released per gram of rock at a temperature between $T_{min}$(° C.) and 600° C. (630° C. on a Humble SR Analyzer).

THC (LV+TD+TC)—Represents the total HC released, including the initial heating and programmed pyrolysis from 180° C. to 600° C. (195° C. to 630° C. on a Humble SR Analyzer) in milligrams of HC released per gram of rock.

$T_{min}$ (° C.)—The temperature at which HC volatilization is at a minimum between the temperature of maximum HC volatilization for TD and TC, and is determined where $\Delta(HC)/\Delta(T) = 0$ and is negative before and positive after. This is the change in hydrocarbon yield over a temperature range, or the derivative. Alternatively, a temperature of 400° C. can be used for samples where there is no discernable minimum between TD and TC. The latter sample types generally have very low total HC yield or high API gravity.

Total Hydrocarbon Index (THI)—Represents the total HC released, including the initial heating and programmed pyrolysis from 195° C. and 630° C., relative to Total Organic Carbon in a sample. The equation for THI is: $THI = [(LV+TD+TC)/TOC] \times 100$.

Total Organic Carbon (TOC)—The TOC is the weight percent of organic carbon found in a rock sample.

Phi ($\Phi$)—The average measured porosity of a rock sample or that assessed by electric logs at a given depth.

Relation to Prior Art Technology

The analytical procedure of the present invention that will be described below is an extension of the analytical methods described in U.S. Pat. No. 5,866,814 and is known as the pyrolytic oil productivity index method, or POPI method. An understanding of this prior art POPI methodology will be useful for practitioners in the field of reservoir characterization and will be briefly summarized below.

Pyrolytic analytical equipment is well known to those familiar with the art. Specific reference will be made below to the Humble SR Analyzer sold by Humble Instruments & Services, Inc. of Humble, Tex., USA and the Rock-Eval™ instrument sold by Vinci Technologies SA of Nanterre, France. The following description includes a number of definitions for terms used in the art followed by a detailed description of the method of the invention and examples of the use of the method.

Pyrolysis: Analytical Procedure

The analytical method used to discern the presence of hydrocarbons is known as open-system pyrolysis. In this type of pyrolysis, a temperature-programmed instrument heats a small amount of a powdered rock sample (usually <100 mg) from a starting temperature of 180° C. (held for 3 minutes) to 600° C. at a rate of 25° C. per minute. During the heating program, the hydrocarbons evolved by the rock sample are recorded as a function of temperature. FIG. 1 shows a typical instrument output plot known as a "pyrogram". A typical sample analysis results in three peaks. The first is composed of hydrocarbons that can be volatilized, desorbed, and detected at or below 180° C. while the temperature is held constant for the first 3 minutes of the procedure. These are called light volatile hydrocarbons (LVHC, or LV).

The next phase of pyrolysis consists of a programmed temperature increase from 180° C. to 600° C. that results in two additional distinct peaks. The first of these occurs between 180° C. and ~400° C., and corresponds to thermal desorption of solvent extractable bitumen, or the light oil fraction. These are called thermally distilled hydrocarbons (TDHC, or TD). The second peak (third peak overall) occurs after about 400° C., generally after a minimum in pyrolytic yield is observed (the temperature corresponding to the minimum in pyrolytic yield is referred to as $T_{min}$) and extends typically to about 550° C. This peak is due to the pyrolysis (cracking) of heavier hydrocarbons (e.g., asphaltenes, pyrobitumen, etc.). The materials that thermally crack are called thermally cracked hydrocarbons or "pyrolyzables" (TCHC, or TC).

Since the development of the pyrolytic oil-productivity, or POPI, method which was based on Rock-Eval™ instruments, other pyrolysis instruments have been manufactured by Humble Instruments. The Humble instruments employ a starting temperature of 195° C., followed by a programmed pyrolysis step from 195° to 630° C. Under these conditions, the two manufacturers' instruments produce equivalent data.

Description of Compositional Modeling Method (CoMod) for Assessing Residual Hydrocarbon Staining Pyrolysis instruments can quantify the amount of hydrocarbon staining and this is the basis for the POPI method of U.S. Pat. No. 5,866,814 which assesses the similarity of residual hydrocarbon staining on reservoir rock to produced oils by subdividing the hydrocarbons into the Light Volatile (LV), Thermally Distillable (TD), and Thermally Crackable (TC) components in accordance with FIG. 1. However, visual inspection of pyrograms can also be used to assess the type of hydrocarbons present because oil, tar, pyrobitumen, and other typical organic matter types have a very characteristic appearance. FIGS. 2a through 2d are pyrograms for samples with a nearly uniform composition of specific hydrocarbon or organic matter end-members. These plots show the hydrocarbon yield on the y-axis for each data step that is recorded on the x-axis.

The number of data steps for a particular analysis can vary based on the type of instrument used, e.g., Vinci's Rock-Eval or Humble's Source Rock Analyzer, and also by how the data are extracted from the machine into a digital file. In the example shown, the Source Rock Analyzer data are output into digital form through a comma separated value (CSV) file that records the yield and temperature over 611 data steps. The first 111 steps record the isothermal hold at 195° C. for 3 minutes and the next 500 steps record the programmed temperature run from 195° C. to 630° C. In general, the temperature associated with any specific step remains the same from analysis to analysis, so the step number is associated with the temperature of the oven during the analysis.

One of the major benefits of the application of pyrolysis methods at well drilling sites has been realized though the compositional modeling method (CoMod) that is described in pending U.S. patent application Ser. No. 10/555,805, the disclosure of which is incorporated herein by reference. This method provides for the identification and quantification of various organic matter "end-members" that are present in a reservoir system and has proved to be extremely robust in assessing the contribution of various organic inputs to pyrolysis results. However, pyrolysis results are expressed in milligrams of hydrocarbon per gram of rock and this standard is not consistent with units from other data sources.

Furthermore, the pyrolysis analytical data can only provide information about the pyrolyzable hydrocarbons. Thus, the weight of pyrolyzable hydrocarbons will routinely differ greatly from the total weight of the organic material, i.e., tar, pyrobitumen, and the like and also from the volume of the material that it represents in the reservoir rock.

The practical usefulness of the pyrolytic methods for reservoir characterization would be enhanced if the data were presented in a form that is meaningful to the intended end-users, e.g., reservoir geologists and engineers. It is desirable to express the pyrolysis results in terms of rock volume for assessing the amounts of various organic components found in reservoir rock, that is, on the basis of either volume per volume or as a percent of rock volume. Adopting preliminary mass-to-volume conversions would significantly improve the usefulness of the data, especially when representing tar and pyrobitumen occurrence and its relative impact on reservoir performance. It would be highly desirable to further refine these conversions in order to make them even more useful.

Compositional modeling for a sample assumes that the yield at each individual data step, which has a specific and consistent temperature associated with it, is a value that is made up of the aggregate yield of the various end-member components. The difference between the modeled yield calculated from the end-member components and the actual yield allows the assessment of the viability of any solution as a representation of the actual composition.

Each solution that is assessed must sum the difference between the calculated yield and the actual yield over all the data steps for the sample. Any of a number of statistical methods can be used in quantifying the overall error for any proposed solution. The modeling relies on iteratively varying the concentration of the various components until the aggregate error is minimized and the curves are as similar as possible. The iterative process of proposing different compositions, calculating a hypothetical curve based on the yield at each data step, assessing the error for each particular solution, and then minimizing this aggregate error can be facilitated through the use of macros and the Solver® add-in application that is present in the Microsoft Excel® software. It is not needed to test solutions, but it greatly automates the process; there are other software packages that can also facilitate the methods used to model hydrocarbon composition.

The modeling process involves varying the percentage of the end-members that are present in the system. Up to five end-members are preferably used for Arabian reservoirs and iterations are applied until the calculated curve matches the actual curve as closely as possible and the error is minimized. Due to the fact that so many calculations must be made to assess any solution, the use of a spreadsheet program to perform these calculations and automatically plot the results is preferred and expedites the processing of data. Moreover, an application such as Solver® that is present as an add-in in Excel® can expedite the process because it is useful for iteratively solving problems with multiple variables that seek to converge on a desired solution, which in this case is minimizing error.

FIG. 3 shows the graphic interface as a plot from Microsoft Excel® for a five-component system in Arabia. The chart includes the program curves for the current sample, the calculated solution based on the percentage of the end-member components, which are identified as the oil end-member, the tar end-member, the shale end-member (typical of dispersed kerogen found in shaley lithologies), the coal end-member, and the drilling mud end-member (contamination). The parameter employed in making the calculations was the Root Mean Square (RMS) deviation as a percent of the total yield and is the value that is minimized in obtaining a reasonable solution for a given sample.

As shown in FIG. 4, when all samples are analyzed for a particular well, the results can be plotted in terms of how the composition varies by percent of each end-member throughout the sampled section. This plot includes oil, tar, shale (or shaley organic matter) and coal. This information is very useful in identifying significant trends, such as increasing tar, or in identifying individual coal or tar units that may have important implications for reservoir performance.

The plot of FIG. 4 does not provide an indication of the amount of material that is represented by the various curves. Another way to view the data is illustrated by FIG. 5, which is a plot of the relative contribution of each component by depth with each curve adjusted for changes in yield in the samples that has been produced by compositional modeling. The data presented in the graphic plot is based on the pyrolytic yield of tar, oil, shaley OM and coal present in the reservoir rock samples. This type of plot is useful for identifying true tar mats that typically have an associated significant increase in hydrocarbon yield expressed in mg HC/g Rock as opposed to a change in composition that appears to be tar, but is present in low amounts and not likely to affect reservoir performance.

While this represents a significant improvement in prior methodologies for reservoir characterization, the data are presented in terms of units that are not utilized by reservoir geologists and engineers, and, therefore, provide only a qualitative assessment of a reservoir that can be difficult to integrate with other analytical and interpretation methods. Moreover, the percentage of pyrolyzable hydrocarbons found in various organic matter types common in reservoir rocks varies widely. For example, residual oil staining that is characteristic of API 30° oil can have a maximum H/C ratio of about 1.9 and total hydrocarbons of about 1190 mg HC/g TOC.

However, due to the presence of resins and asphaltenes, the maximum observed is only around 1050 mg HC/g TOC. Tar, which has a much lower H/C ratio (accepted values ranging from 1.4 to 0.8), will typically have total hydrocarbons that yield between 700 to 400 mg HC per gram of TOC; pyrobitumen, can have a total hydrocarbon content that is only ~200 mg of HC per gram of TOC. Thus, 5 mg of oil would give the same pyrolytic yield (THC) as about 10 mg of tar and about 25 mg of pyrobitumen. Given the magnitude of these differences, the difficulty of interpreting pyrolysis data based on yield is evident.

Hydrocarbon Measurement of Organic Matter via Pyrolysis and FID

Organic matter found in oil reservoirs can consist of oil (crude oil), heavy oil, tar, pyrobitumen, and, sometimes, minor amounts of kerogen, coal or recycled organic matter. In the context of SARA analysis, the term "hydrocarbons" in a reservoir consist of only the saturate and aromatic fractions that are obtained from these materials via chemical group type separation. SARA analysis results are reported in terms of saturate, aromatic, resin, and asphaltene fractions, of which, the saturate and aromatic fractions are considered hydrocarbons and the resin and asphaltene fractions are considered non-hydrocarbons. In addition, these terms can be used to describe the soluble portion of the organic matter, since coal, kerogen and pyrobitumen are largely insoluble if found as a "near" end-member, whereas the insoluble portions obtained through extraction and de-mineralization procedures are exclusively non-hydrocarbons.

The primary detector used to analyze "hydrocarbons" in petroleum geochemistry, especially for gas chromatography and pyrolysis applications is the flame ionization detector (FID). The flame ionization detector is commonly considered to be a "carbon counting device" and relies on an "equal per carbon response." Although flame ionization detectors are used to assess the quantities of "hydrocarbons," they do not distinguish between "pure" hydrocarbons, as found in saturate and aromatic fractions from SARA analysis, and hydrocarbon "units" that occur as part of the molecular structure in non-hydrocarbon compounds that range from relatively simple structures containing "non-hydrocarbon" functional groups to very complicated molecules and large molecules that comprise asphaltenes, kerogen and the like.

As noted above, hydrocarbon pyrolysis is employed to liberate hydrocarbons and compounds containing hydrocarbon structural units before they are measured by a flame ionization detector (FID). At temperatures below ~400° C., the organic compounds are volatilized or desorbed from the rock primarily without cracking into smaller units. Above ~400° C., the organic compounds that are liberated are mainly the result of cracking larger molecules into smaller components that are carried to the FID and measured. However, pyrolysis is an incomplete process that results most often in the detection of only a portion of the material that is being analyzed. Therefore, the organic material can be described as being either "pyrolyzable" or "non-pyrolyzable", on the basis of whether or not the result of the process can be measured by the FID.

As used herein, a reference to hydrocarbons means compounds, or portions of compounds that have hydrocarbon units with the formula of $C_nH_{xn}$, where n is the number of carbon atoms and x is the number of hydrogen atoms per carbon atom. This is a functional definition based on the fact that a flame ionization detector (FID) is used to assess their quantity. However, it is important to note that the carbon atoms that are linked to heteroatoms (i.e., N, S, and O) often do not provide an "equal per carbon number" (ECN) response. See Holm, J. Chromatography, 842, pp. 221-227 (1999). Thus, the heteroatoms present in non-hydrocarbons will result in relative under-reporting of the "hydrocarbon" response and calculations of the amount of hydrogen and carbon based on this response should yield somewhat lower percentages than obtained from elemental analysis.

Due to these effects, the utilization of pyrolysis and FID to measure hydrocarbon structural units will inherently result in an under-reporting of hydrogen and carbon when the data are compared to elemental analysis data. However, it is important to note that while elemental analysis may be the most definitive test that can be undertaken to assess the organic matter in a sample, the tests are very time-consuming, expensive, and subject to numerous errors, thereby requiring multiple tests. The complexity of sample preparation (e.g., mineral separation and extractions), and the weighing of small samples add to the difficulties of the elemental analytical method.

SUMMARY OF THE INVENTION

The volume of organic matter (VOM) method provides a novel solution to the complicated problem of directly measuring the weight or volume of tar or pyrobitumen in reservoir rock. The method has the following advantages: (1) it relies on direct measurement of hydrocarbons; (2) it utilizes relatively simple and robust analytical techniques that can be applied quickly and inexpensively; and (3) the determination of physical properties of end-member components is based on a relatively few samples. The modeling of pyrolysis data provides a quick and effective means of analyzing a large number of samples by separating complex mixtures for each sample, determining their composite characteristics, and providing quantitative data concerning the amount of various materials by weight and volume in a reservoir.

A further important advantage of the VOM method of the invention is that it provides geochemical data in measurement units that can be readily related to reservoir performance by non-geochemists. This advantage has not been provided by other geochemical tools of the prior art that are commonly used to assist in reservoir characterization.

As noted above, the residual hydrocarbon staining found on reservoir rock is composed of materials with very different properties and amounts, and simple relationships that depend principally on pyrolytic yield are not effective in characterizing the organic matter. For example, in a reservoir being assessed for tar occlusion of porosity, the amount of tar relative to pyrobitumen is typically different in each sample analyzed. Assessing the amount of pore plugging based on a simple conversion of yield to volume would therefore rely on an ever-changing conversion factor.

The compositional modeling (CoMod) method resolves the problem of sample variation. Although the materials that are being quantified vary widely in characteristics and their analysis is through the simple means of FID, CoMod provides a very accurate discrimination of the relative input of these materials based on the differences that are observed in typical pyrograms. Since the end-member organic components exhibit characteristics that are fairly consistent within a reservoir, results from CoMod, pyrolytic yields, and organic matter properties can be combined to determine the representative volume of various organic matter types found in a reservoir, including most importantly, tar and pyrobitumen.

The steps in the application of the volume of organic matter (VOM) method of the invention include the following:

1. Collect rock samples, prepare for analysis by POPI/AS$_w$ method, and analyze to obtain raw data for each sample that includes, comma separated value (CSV) files consisting of step, temperature, and incremental FID response or HC yield.
2. Determine the appropriate local organic matter end-members to employ in compositional modeling, e.g., oil, tar, pyrobitumen, coal, kerogen, diesel, mud contaminants and any other locally significant components.
3. Perform the compositional modeling to determine the relative hydrocarbon yields (mg HC/g rock) for each end-member sample that was analyzed.
4. Obtain physical/chemical properties of organic matter end-members.
5. Develop the relationship between the pyrolytic yield and mass/volume for each end-member material.
6. Analyze non-end-member samples from the well under study and obtain raw data as described above.
7. Determine the mass and volume for each end-member in all samples. This can be done in real-time and, in a preferred embodiment, reported directly from the wellsite so that the results can be used as input for geosteering horizontal wells.
8. Use the matrix density, grain density and porosity to determine the volume percentages of each end-member in all samples.
9. Prepare graphic plots of the volume of end-members found in each sample as a function of depth and relate the data to reservoir porosity.
10. Integrate the results from the VOM method analysis with well logs and dynamic test results such as DSTs, MDTs, Flow Meters, and GEOTAP to assess how much immovable hydrocarbon (relative to reservoir porosity) is needed to have a detrimental effect on reservoir performance objectives.

BRIEF DESCRIPTION OF THE DRAWINGS

The invention will further be described and placed in the context of the prior art with reference to attached drawings in which.

DETAILED DESCRIPTION OF THE INVENTION

Figure 1:
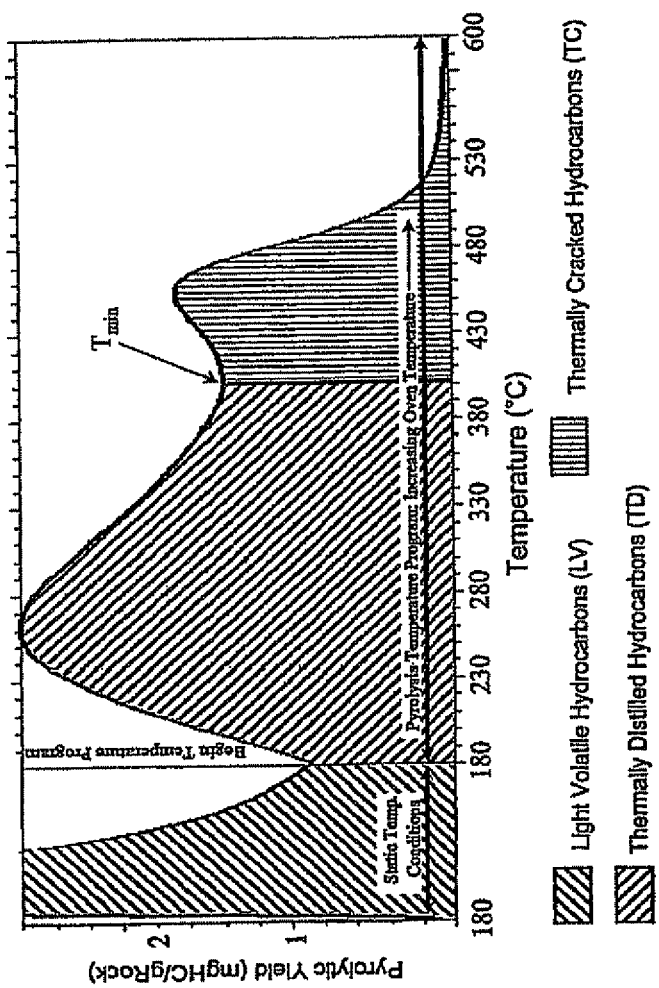
FIG. 1 is a typical output pyrogram of the prior art from an instrument performing open-system temperature programmed pyrolysis.
Figure 2A:
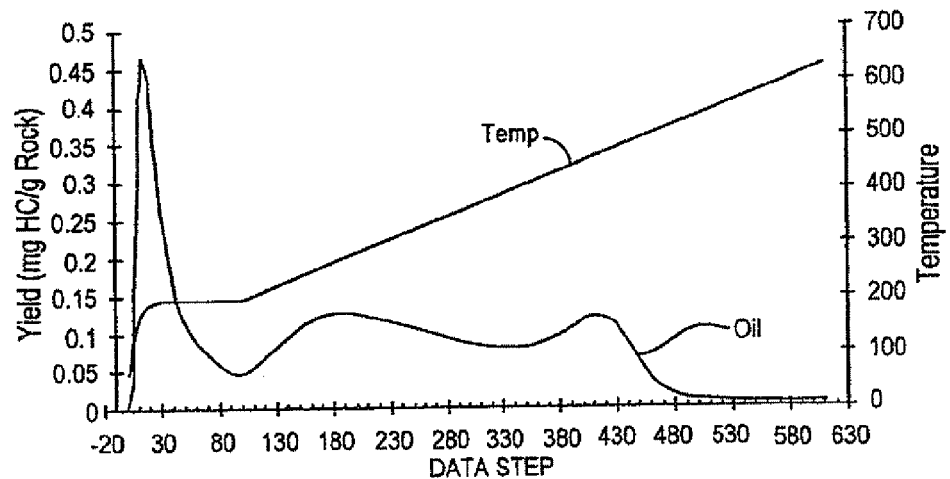
FIG. 2(a) is a typical prior art pyrogram of API 30° oil from an Arabian reservoir.
Figure 2B:
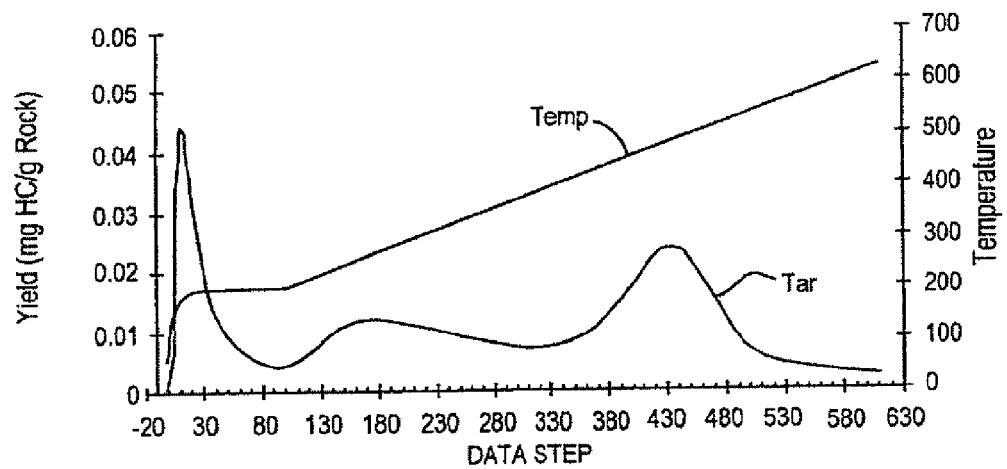
FIG. 2(b) is a typical prior art pyrogram of tar from an Arabian field.
Figure 2C:
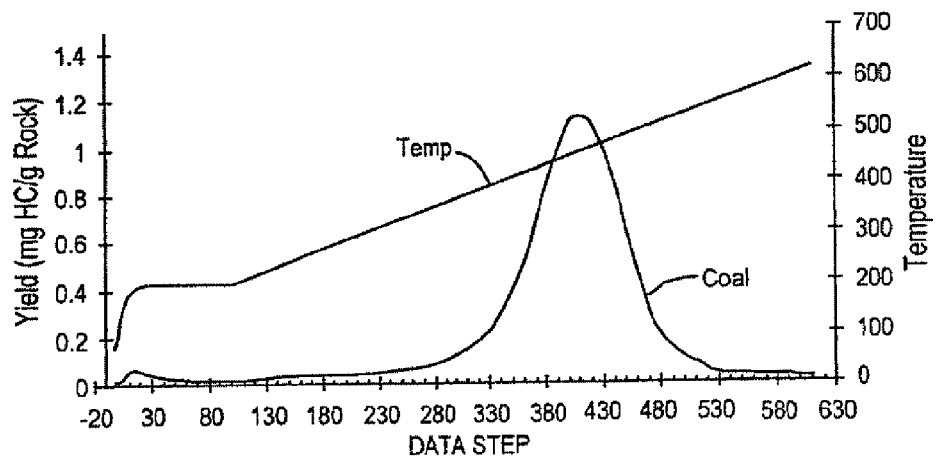
FIG. 2(c) is a typical prior art pyrogram of coaly organic matter from the Arabian field.
Figure 2D:
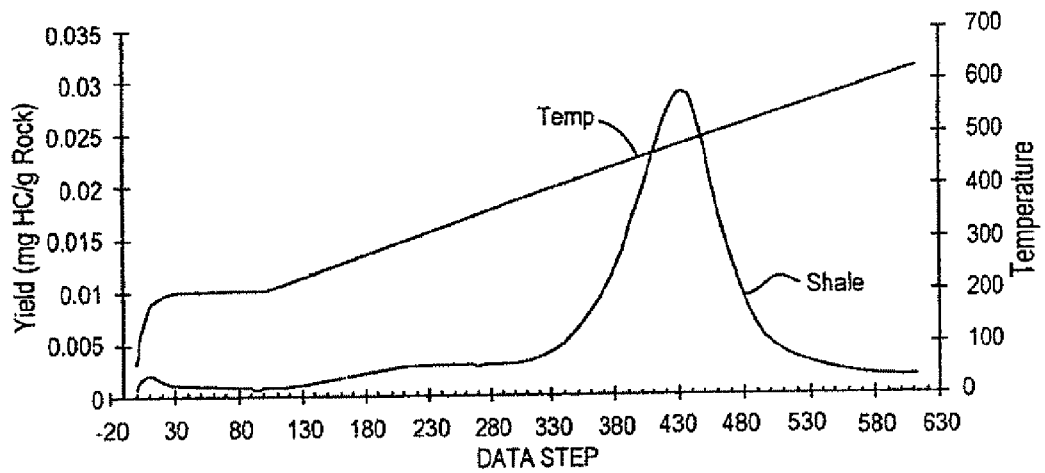
FIG. 2(d) is a typical prior art pyrogram of organic-rich shale from the same Arabian field.
Figure 3:
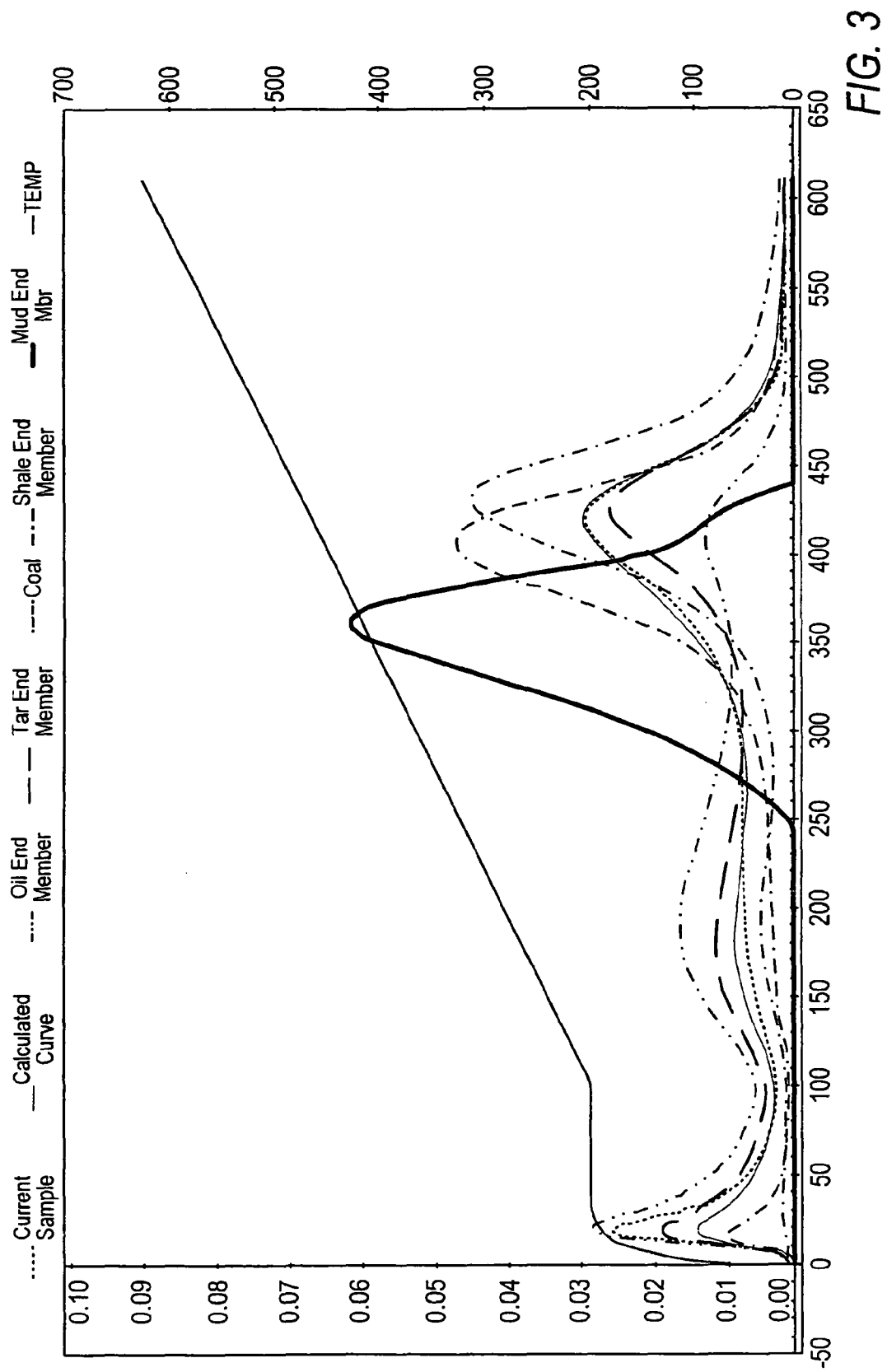
FIG. 3 is a graphical plot produced using Microsoft Excel® showing the compositional modeling interface developed to perform the calculations in accordance with the invention in which the plot shows pyrograms associated with the sample, a calculated solution and end-members that are used in the modeling process.
Figure 4:
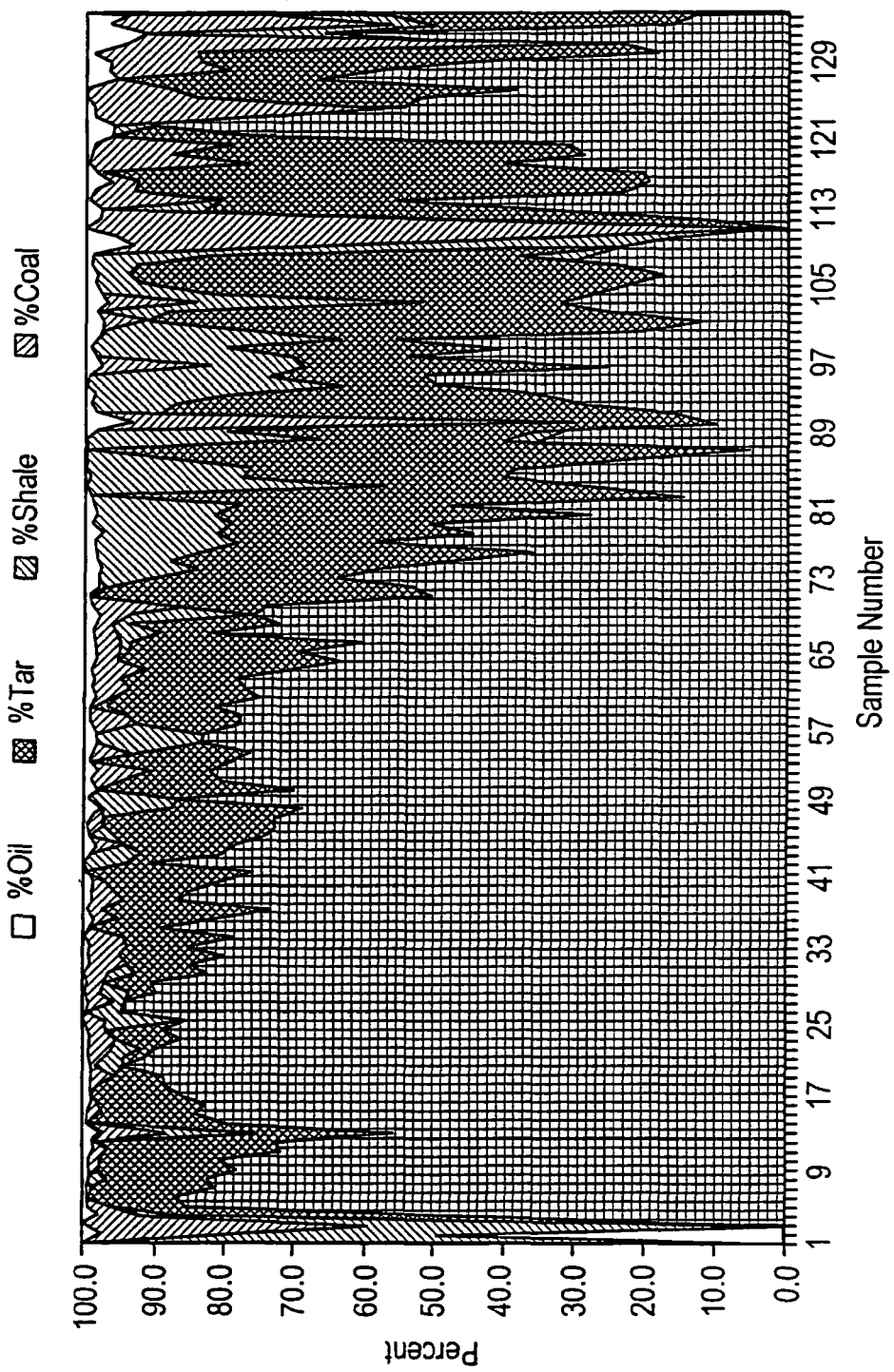
FIG. 4 graphically displays the results from compositional modeling for a well in the Arabian field showing the percentage of oil, tar, shaley organic material and coal present in reservoir rock samples tested.
Figure 5:
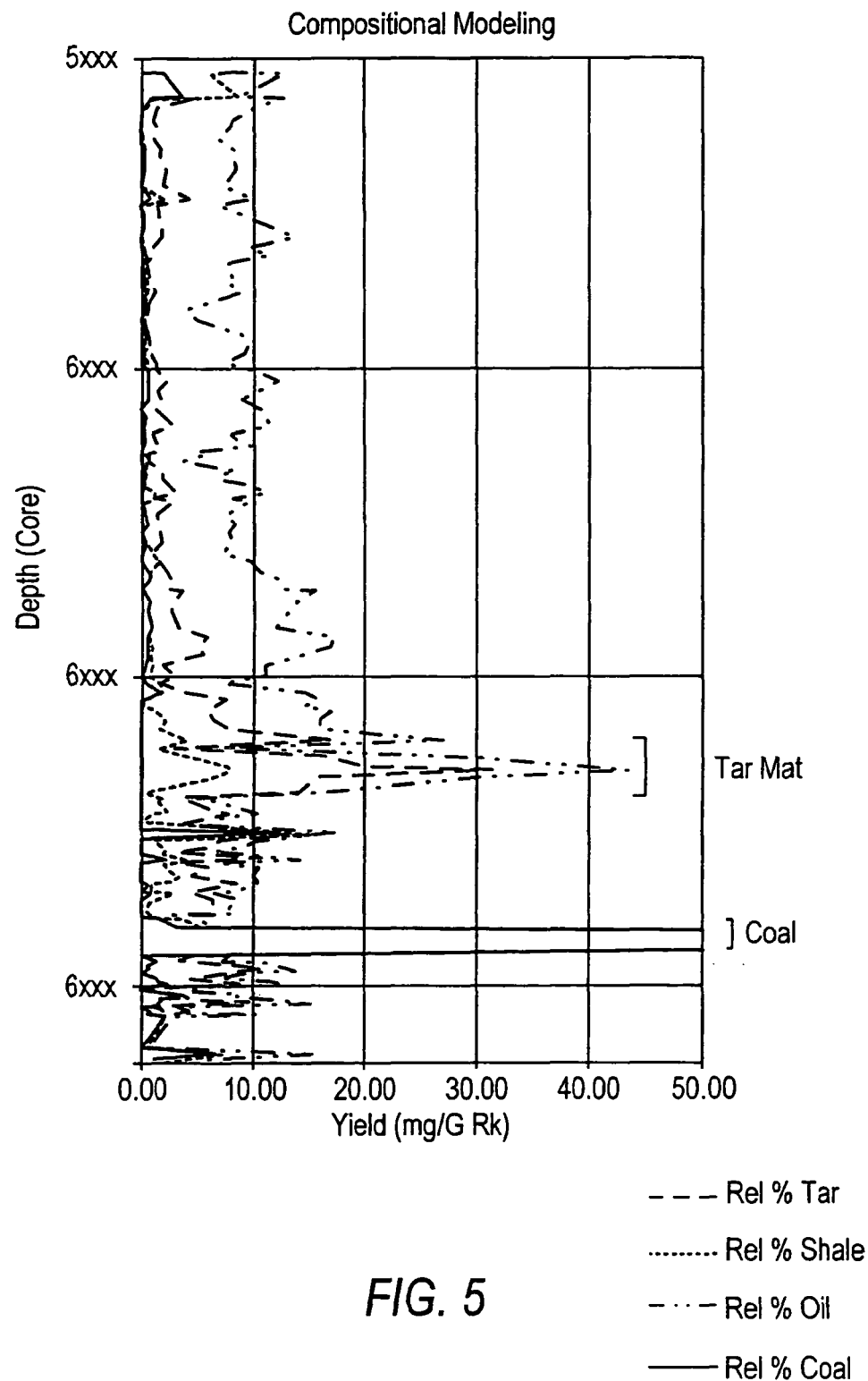
FIG. 5 graphically displays the results from compositional modeling for a well in the Arabian field showing the relative pyrolytic yield of oil, tar, shaley organic material and coal present in the samples at varying depths and illustrates how hydrocarbon yield increased significantly in true tar mats and coal beds.

The methods employed in steps 1-3 above are the same as those described in U.S. Pat. Nos. 5,866,814 and 6,823,298, and will not be further described here. A detailed description of the remaining steps employed in the practice of the VOM method of the invention are provided below.

Determination of Physical and Chemical Properties of End-Members

The compositional modeling (CoMod) method is effective for determining the percentage of various organic end-members in the total mixture of hydrocarbons in a sample as determined by pyrolysis. However, in order to predict the volume of tar and pyrobitumen in oil reservoirs, the results from CoMod must be combined with relationships that allow the total weight or volume of material to be determined based on the weight of the hydrocarbon portion as indicated by the FID of the pyrolysis instrument.

Organic matter, such as oil, tar, pyrobitumen, kerogen, and the like found in petroleum systems is typically composed of "pure" hydrocarbons, i.e., saturate and aromatic fractions from chemical group type separations (SARA) that only contain carbon and hydrogen atoms; nitrogen, sulfur, and oxygen compounds, i.e., resins and asphaltenes from SARA; inert carbon; and trace amounts of nickel, vanadium, aluminum and silicon. Alternatively, the composition of petroleum and related compounds can be calculated by elemental analysis, i.e., percentages of carbon, hydrogen, nitrogen, oxygen and others. Neither the physical segregation and analysis of petroleum materials, nor their elemental analysis can be applied routinely on a large number of samples. However, geochemical instruments such as Humble Instrument's SR Analyzer—POPI/TOC Workstation or Vinci's Rock-Eval™ 6 Analyzer can provide routine information regarding the quantity of hydrocarbons, or the hydrocarbon response as assessed by FID relative to the total quantity of carbon found in samples. With this information and a limited amount of elemental data for percentages of C, H, N, O and S, the amount of tar or pyrobitumen can be related to the total hydrocarbon yield.

The following equations are representative of the relationship:

$$\text{Mass}_{Tar} = \text{Mass}_{\text{"pure"}HC} + \text{Mass}_{Cinert} + \text{Mass}_{CHNSOs} + \text{Mass}_{Ni,V,Al,Si} \quad (1)$$

$$\text{Mass}_{Tar} = \text{Mass}_C + \text{Mass}_H + \text{Mass}_N + \text{Mass}_S + \text{Mass}_O + \text{Mass}_{Ni,V,Al,S} \quad (2)$$

where $\text{Mass}_{Tar}$ is equal to the actual Mass of tar; $\text{Mass}_{\text{"pure"}HC}$ is equal to the mass of hydrocarbon structural units that can be pyrolyzed and measured by FID; $\text{Mass}_{Cinert}$ is equal to the mass of inert carbon that cannot be analyzed by FID; $\text{Mass}_{CHNSOs}$ is equal to the mass of carbon-containing functional groups that are not measured or are underestimated by pyrolysis-FID measurement; $\text{Mass}_{Ni,V,Al,Si}$ is the mass of trace elements present in tar, such as nickel, vanadium, aluminum, silicon, and others, that not measurable by FID; $\text{Mass}_C$ is equal to the mass of elemental carbon as determined by elemental analysis; $\text{Mass}_H$ is equal to the mass of elemental hydrogen as determined by elemental analysis; $\text{Mass}_N$ is equal to the Mass of elemental nitrogen as determined by elemental analysis; $\text{Mass}_S$ is the mass of elemental sulfur as determined by elemental analysis; $\text{Mass}_O$ is the mass of elemental oxygen as determined by elemental analysis and $\text{Mass}_{Ni,V,Al,Si}$ is the mass of trace elements as determined by elemental analysis.

As will be understood by one of ordinary skill in the art, the quantities represented by the trace elements are very small and can be disregarded for the purpose of assessing weights and volumes of organic matter in petroleum reservoirs. Second, the test results of either the Rock Eval 6 or the POPI/TOC Workstation can provide the total hydrocarbon yield and the total amount of carbon in a sample. The results obtained from the elemental analysis of a few samples from the separated end-members and the application of reasoned assumptions regarding average stoichiometry of hydrocarbons are used to determine the relationships for estimating the total mass/volume of end-member materials from the hydrocarbon yield data.

The most significant variation found in the several organic matter end-members of a petroleum reservoir system is the amount of hydrogen present. A parameter commonly used in the assessment of petroleum source rocks is the Hydrogen Index (HI), which describes the generative potential of source rock through a ratio of the amount of "pyrolyzable" hydrocarbon bound in the kerogen ($S_2$, mg HC/g Rock) of a rock sample to the amount of total organic carbon (TOC). It is expressed as HI=($S_2$/TOC)×100, which provides units of mg of hydrocarbon per gram of carbon. (See Peters, AAPG Bulletin, vol. 70, pp. 318-329, 1986.) This relationship does not account for the "free" hydrocarbons that are already present in a sample by using only the hydrocarbons detected at temperatures above 300° C.

In the assessment of reservoir rock samples, the goal is to characterize all of the hydrocarbons, whether they are "free" hydrocarbons or those bound in a complex structure. In addition, the methods differ in that the analytical procedure utilizes a starting temperature that is much lower (180° to 195° C.). Nonetheless, for each end-member, e.g., oil, tar, pyrobitumen, the amount of hydrocarbon by pyrolysis per gram of carbon will be fairly consistent. This parameter is referred to as the Total Hydrocarbon Index (THI) and is calculated as follows:

$$THI=[(LV+TD+TC)/TOC]\times 100 \quad (3)$$

The units for THI are the same as HI, i.e., mg of hydrocarbon per gram of organic carbon. The Rock-Eval 6 or Humble POPI/TOC analyzers can be used to assess the differences in hydrogen for various end-members. THI is a ratio, with both TOC and THC (LV+TD+TC) determined during the same analysis, thus the errors associated with isolation of the OM, weighing, and small sample sizes that can occur in elemental analysis do not affect the data. It is important that sufficient separations of the organic end-members be obtained, so that results are consistent. Additional information that is needed for each organic matter end-member are the results from elemental analysis, i.e., as would be obtained from a CHNOS analyzer. With the percentage amounts of these elements and THI, the average amount of hydrogen present in the pyrolyzable and non-pyrolyzable portions of end-members can be determined in order to calculate the weight of the overall material. As stated above, the presence of heteroatoms in the various end-members and incomplete pyrolysis does result in some under-reporting of the quantity of hydrocarbon structural units based on the FID response. However, these effects are treated as contributing to the same result when assessing the pyrolyzable versus non-pyrolyzable portion of organic matter.

A typical separation of organic material in reservoir rock can be accomplished through a series of extraction/analytical steps. It is desirable to analyze the produced oil, which can be measured by placing a few microliters of oil on silica gel in a crucible and drying it in an oven at 30° C. for about 6 hours to remove the volatile components. The results of this analysis, plus CHNOS on the oil, provide a means for calculating the mass of oil per gram of rock contained in a sample. Another way of assessing the oil fraction is to extract the rock sample with cyclohexane. The extract that is obtained from this procedure will typically resemble the moveable hydrocarbons in the reservoir and the subsequent measurement of THI and CHNOS will provide data that are suitable for VOM analysis. In addition to the measurement of parameters for the extract, the THI and CHNOS data are also measured on the rock extracted with cyclohexane. This data represents the "immovable" bitumen remaining on the rock after cyclohexane extraction.

The next step in the process is to perform a second extraction on the cyclohexane extracted rock using a strong polar solvent, such as methylene chloride. The resulting extract is considered typical of the remaining tar or asphaltene component of the hydrocarbon staining, while the residual organic matter left in the rock consist of either pyrobitumen (tar that has been altered, lost a significant portion of its hydrogen, and become insoluble even in strong organic solvents) or another insoluble material like coal or kerogen. A variety of mechanisms have been proposed for the formation of pyrobitumen, including thermochemical sulfate reduction (TSR) and thermal alteration. However, there is no single accepted pathway. Nonetheless, hydrogen content in pyrobitumen is lower and the yield of hydrocarbon per gram of carbon is also lower. As with the cyclohexane extract and remaining rock, the methylene chloride extract and methylene chloride extracted rock are both analyzed by pyrolysis to determine the THI, and by elemental analysis for the CHNOS composition of the samples.

Determining Pyrolytic Yield and Mass/Volume Relationship for End-Members

The use of pyrolysis data to determine the volume of various organic constituents in the residual hydrocarbon staining is based on the determination of the Total Hydrocarbon Index for various reservoir organic matter (OM) types and the results from the previously described compositional modeling (CoMod) method. Detailed analysis of the end-members present in a reservoir is only needed for a limited number of samples in order to develop a relationship between the weight of the hydrocarbon component and the total weight of an end-member. Table 1 illustrates in tabular form the calculation steps required to develop the conversion factors for oil, tar and pyrobitumen and their application to determine the volume of end-members in conjunction with CoMod results. Since THI is based on the mg of hydrocarbon per gram of TOC, the composition of the end-members is also given relative to one gram of TOC. In addition, since pyrolysis instruments assess the weight of hydrocarbon in terms of mg per gram of rock, the amount of rock matrix assumed in this calculation is also 1 gram.

In this example, the results from Rock Eval 6 for this reservoir provide a THI of 1050, 525, and 250 respectively for the oil, tar, and pyrobitumen end-members. The results from elemental CHNOS analysis indicate that the end-members have $H/C_{OM}$ ratios of 1.9, 1.05, and 0.65, respectively, for oil, tar and pyrobitumen. Because the calculations are based on 1 gram of carbon, the weight of hydrogen in the organic matter based on elemental analysis in the sample can be calculated as follows:

$$\text{Wt. } H_{OM}(\text{mg}/1 \text{ g TOC})=H/C_{OM}\times(1000 \text{ mg C/Mol. Wt.}_{Carbon}) \quad (4)$$

As stated previously, utilization of the combined pyrolysis and FID method results in the under-reporting of the weight-percent of hydrogen, because some of the hydrogen is associated with the pyrolyzable OM and some is associated with the non-pyrolyzable OM. Because the aliphatic bonds in complex molecules like asphaltenes and kerogen are most readily broken, it is assumed that the stoichiometry of aliphatic structural units, i.e., $-C_nH_{2n}$, are dominant in the pyrolyzable portion of the organic matter. This results in an average weight-percent for hydrogen in the pyrolyzable hydrocarbons (% H $C_nH_{2n}$) of 14.3%. Applying this assumption, the weight of hydrogen in the pyrolyzable hydrocarbons is determined as follows:

$$\text{Wt. } H_{HCPy}(\text{mg/1 g TOC}) = \% \text{ H } C_nH_{2n}/100 \times \text{THI(mg HC/g TOC)} \times 1 \text{ g TOC} \quad (5)$$

The weight of hydrogen in non-pyrolyzable OM is determined as follows:

$$\text{Wt. } H_{Non-Py}(\text{mg/1 g TOC}) = \text{Wt. } H_{OM}(\text{mg/1 g TOC}) - \text{Wt. } H_{HCPy}(\text{mg/1 g TOC}) \quad (6)$$

In accordance with the method of the present invention, the weights of hydrogen in the non-pyrolyzable portion of oil, tar and pyrobitumen for this example are 8.2 (mg/1 g TOC), 12.4 (mg/1 g TOC), and 18.4 (mg/1 g TOC), respectively. Thus, the assumption that the hydrocarbon liberated from organic matter by pyrolysis is dominated by aliphatic units results in an under-reporting of hydrogen that is relatively large for tar (14.2%) and even larger for pyrobitumen (34%). Moreover, assuming that the average composition of the measured hydrocarbons from pyrolysis-FID has a lower H/C ratio, would only increase the hydrogen under-reporting from pyrolysis, which would necessitate a larger correction.

In order to simplify the approach, in the method of the invention the $-C_nH_{2n}-$ structural units are assumed to be the dominant form that is produced by pyrolysis of organic matter from petroleum reservoirs. However, it should be noted that the error involved in misrepresenting the amount of hydrogen in the sample is relatively small. For example, the 18.4 mg H/1 g TOC under-reporting for hydrogen in pyrobitumen would result in only a 1.75% error if totally disregarded. When the purpose of the calculations is to assess the volume of tar in a reservoir, and the critical amount of tar present is around 5% of the volume, it will be understood that the difference between 4.9% and 5.1% tar by volume is not significant.

Once the respective weights for hydrogen in the sample have been determined, the weight of carbon in the pyrolyzable OM and non-pyrolyzable OM can be calculated as follows:

$$\text{Wt. } C_{HCPy}(\text{mg/1 g TOC}) = \text{THI(mg/1 g TOC)} \times 1 \text{ g TOC} - \text{Wt. } H_{HCPy}(\text{mg/1 g TOC}) \quad (7)$$

$$\text{Wt. } C_{Non-Py}(\text{mg/1 g TOC}) = 1000 \text{ mg TOC} - \text{Wt. } C_{HCPy}(\text{mg/1 g TOC}) \quad (8)$$

The elemental composition analysis of crude oils shows that elemental N, S, O typically comprise between 1-4% and asphaltene fractions will typically range from 5-12%. In the present example, the NSO values determined for the oil, tar and pyrobitumen were 2.8%, 7.3%, and 7.6%, respectively, which is within the range noted in the literature see (Ancheyta, et al., Energy and Fuels, Vol. 16, pp 1121-27, 2002; Holleran, VSS Technology Library, Valley Slurry Seal Company, www.slurry.com/techpapers contrbit.shtml, 2000). Thus, from CHNOS elemental analysis, the weight-percent attributed to elemental nitrogen, sulfur and oxygen in the sample can be readily determined. Once these values have been determined, the weight of this material in the organic end-member can be calculated as follows:

$$\text{Wt. } NSO_{OM} = \frac{(\% NSO_{OM}/100) \times (\text{Wt. } C_{HCPy} + \text{Wt. } C_{Non-Py} + \text{Wt. } H_{HCPy} + \text{Wt. } H_{Non-Py})}{(1 - (\% NSO_{OM}/100))} \quad (9)$$

The total weight of organic matter for each end-member can be calculated relative to 1 gram of TOC and the ratio of organic matter to pyrolyzable hydrocarbon (OM/HC$_{Py}$) can be determined as follows:

$$\text{Wt. OM(mg/1 g TOC)} = \text{Wt. } H_{HCPy} + \text{Wt. } H_{Non-Py} + \text{Wt. } C_{HCPy} + \text{Wt. } C_{Non-Py} + \text{Wt. } NSO_{OM} \quad (10)$$

$$\text{OM/HC}_{Py} = \text{Wt. OM/THI, or} \quad (11)$$

$$\text{OM/HC}_{Py} = \text{Wt. OM}/(\text{Wt. } H_{HCPy} + \text{Wt. } C_{HCPy}) \quad (12)$$

As with the weight of hydrogen in the sample, variations in the amount of elemental N, S, O in organic matter within a reservoir are not likely to affect the estimated volume of organic matter by more than a few percent. It is important to determine suitable end-members that produce accurate CoMod results. Since OM/HC$_{Py}$ ratios for the example shown were 1.13 for oil, 2.23 for tar, and 4.56 for pyrobitumen, errors in the modeling process are far more important than minor errors associated with the chemical make-up of these materials. Therefore, it is particularly important to confirm modeled results with laboratory separations that show that the relative amount of soluble versus insoluble materials is similar. This is because a 5% volume of pyrobitumen has a response that is equal to about 2.5% volume of tar.

Determination of Mass and Volume for End-Members in Analyzed Samples

The determination of the weight of each end-member is readily calculated from the results of CoMod in combination with the relevant OM/HC$_{Py}$ ratio. As with other weights, the results are expressed in units of milligrams per gram of rock. The equations that are applied for this step are as follows:

$$\text{Wt. } HC_{End\text{-}Member(X)} = THC_{(X)} \times \% \text{ CoMod Yield}_{End\text{-}Member(X)} \quad (13)$$

$$\text{Wt. } OM_{End\text{-}Member(X)} = OM/HC_{Py} \times \text{Wt. } HC_{End\text{-}Member(X)} \quad (14)$$

The determination of the volume of each end-member is then obtained by dividing the mass of the end-member for a sample by the density of the end-member. The range in the density of organic matter that is commonly found in petroleum reservoir systems is fairly narrow.

Oil density in the industry is measured in units of API Gravity. API Gravity is calculated by the following standard equation:

$$\text{API} = (141.5/\text{SG at } 60° \text{ F.}) - 131.5, \quad (15)$$

where SG is the specific gravity of the fluid at 60° F. Therefore, in this example, 30° API Gravity oil has a density of 0.9 grams/cm$^3$, which can be also expressed as 0.9 mg/µl. The density range for tar and pyrobitumen is generally between 1.0 and 1.15 mg/µl. The occurrence in oil reservoirs of tar with a density approaching or exceeding 1.15 mg/µl is not common because the typical density of the formation water is about 1.15 mg/µl. In order for tar to accumulate in the oil column by a normal emplacement mechanism, the tar should be lighter than formation water; however, the density could be subject to change based on alteration of the material after emplacement. In any case, the values used in this example are consistent with the above constraints, with oil, tar and pyrobitumen having densities of 0.9, 1.01, and 1.05 respectively. Utilizing these values, the volume of the end-members for the sample can be calculated as follows:

$$\text{Volume OM}_{End\text{-}Member(X)} = \text{Wt. OM}_{End\text{-}Member(X)} / \text{Density}_{OM} \quad (16)$$

Determination of Volume in Terms of the Percent of Rock Volume

In order to relate the volume of organic matter end-members, such as tar or pyrobitumen, to the total rock volume, the matrix density and the associated porosity of the reservoir at the sample depth must be known. If a well is being analyzed while drilling, an average porosity can be used over sections of the well with acceptable results; however, large changes in reservoir porosity can result in understating or overstating the amount of tar in the reservoir with respect to volume. The equation for reservoir porosity is as follows:

$$\text{Phi}(\Phi) = [(\text{bulk volume} - \text{rock volume})/\text{bulk volume}] \times 100 \quad (17)$$

Since the data from pyrolysis are presented in mg HC/g Rock, the volume of OM for the end-members can be related to porosity by determining the bulk volume of rock and the volume of the end-member that is associated with 1 gram of rock. The bulk volume of the reservoir can be related to matrix density and porosity as follows:

$$\text{Bulk Volume}(\mu l) = 1/(\text{matrix density} - (\text{matrix density} \times \Phi/100)) \times 1000 \quad (18)$$

In the example of Table 1, the matrix density is 2.71 mg/μl, which is the value for limestone. The porosity was 15%, and the respective volume of end-members for this sample is 1.0% oil, 2.6% tar, and 2.9% pyrobitumen.

Figure 6:
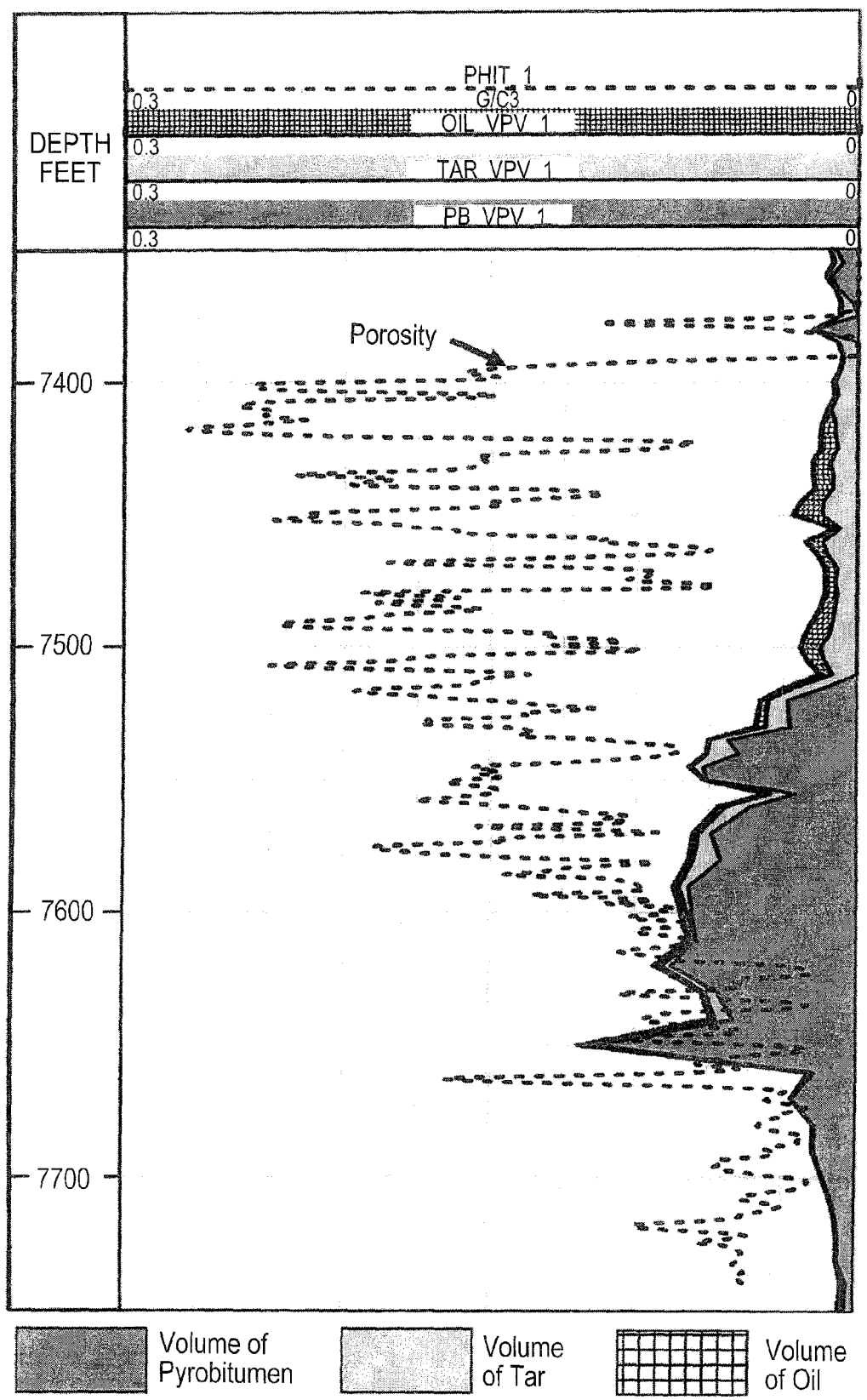
FIG. 6 is a plot of VOM results and porosity vs. depth.

Prepare Plots of Volume of End-Member Components and Reservoir Porosity versus Depth Referring to FIG. 6, a plot of the volume of end-members in relation to reservoir porosity versus depth is illustrated. The samples were obtained from drill cuttings and the depth cannot be as accurately determined as with core samples. VOM results presented in the plot include: Volume of Oil (OIL_VPV_1; hatched pattern fill), Volume of Tar (TAR_VPV_1; light gray fill), and Volume of Pyrobitumen (PB_VPV_1; dark grey fill). Reservoir Porosity is shown by the dotted curve (PHIT).

The results of the VOM analysis clearly places the top of a tar mat in the reservoir at ~7,510 ft. and indicates that it is composed primarily of pyrobitumen. In relating these results to the porosity (PHIT), VOM analysis shows that the tar mat occludes 40-100% of the available porosity. The plot is particularly useful since it presents VOM results in a scale that can be compared directly to the important reservoir parameter of porosity. A reservoir geologist or

TABLE 1

Illustration of calculation steps required to develop conversion factors relating total hydrocarbon yield to the volume of organic matter as a percent of rock volume.

Physical and Chemical Properties of OM

|  | Wt $C_{OM}$ (mg) | $THI_{OMPy}$ | $H/C_{OM}$ (From CHNOS) | % H $C_nH_{2n}$ | Wt. H (From CHNOS) | Wt. $H_{HCPy}$ (mg/1 g TOC) | Wt. $H_{Non\text{-}Py}$ (mg/1 g TOC) |
|---|---|---|---|---|---|---|---|
| Oil 30° API | 1000 | 1050 | 1.90 | 14.3 | 158.3 | 150.2 | 8.2 |
| Tar | 1000 | 525 | 1.05 | 14.3 | 87.5 | 75.1 | 12.4 |
| Pyrobitumen | 1000 | 250 | 0.65 | 14.3 | 54.2 | 35.8 | 18.4 |

|  | Wt. $C_{HCPy}$ (mg/1 g TOC) | Wt. $C_{Non\text{-}Py}$ (mg/1 g TOC) | % Elemental N, S, $O_{OM}$ (From CHNOS) | Wt. Elemental $NSO_{OM}$ (mg/1 g TOC) | Wt. OM (mg/1 g TOC) | $OM/HC_{Py}$ |
|---|---|---|---|---|---|---|
| Oil 30° API | 899.9 | 100.2 | 2.80% | 33 | 1192 | 1.13 |
| Tar | 449.9 | 550.1 | 7.30% | 86 | 1173 | 2.23 |
| Pyrobitumen | 214.3 | 785.8 | 7.60% | 87 | 1141 | 4.56 |

Volume of Organic Matter Determination

|  | $THC_{Py}$ (mg/g Rock) | CoMod | Wt. $HC_{Py}$ (mg/g Rock) | Wt. OM (mg/g Rock) | Den OM (mg/μl) | Vol. OM (μl/g Rock) |
|---|---|---|---|---|---|---|
| Oil 30° API | 11.5 | 30% | 3.45 | 3.92 | 0.9 | 4.35 |
| Tar | 11.5 | 45% | 5.18 | 11.56 | 1.01 | 11.45 |
| Pyrobitumen | 11.5 | 25% | 2.88 | 13.12 | 1.05 | 12.50 |

|  | Matrix Density (mg/μl) | Porosity | Bulk Volume 1 g Rock (μl) | Pore Volume 1 g Rock (μl) | Volume of OM (% Rock Vol.) |
|---|---|---|---|---|---|
| Oil 30° API | 2.71 | 15.0 | 434 | 65 | 1.0% |
| Tar | 2.71 | 15.0 | 434 | 65 | 2.6% |
| Pyrobitumen | 2.71 | 15.0 | 434 | 65 | 2.9% |

Wt $C_{OM}$ (mg)—Weight of Carbon in Organic Matter (OM)
$THI_{OMPy}$—Total Hydrocarbon Index by Pyrolysis
$H/C_{OM}$ From CHNOS—Atomic H/C Ratio in Organic Matter
% H $C_nH_{2n}$—Wt. Percent Hydrogen in Alkane Structural Units
Wt. H (From CHNOS)—Calculated wt. of Hydrogen from Elemental Analysis
Wt. $H_{HCPy}$ (mg/1 g TOC)—Weight of Hydrogen in Pyrolyzable HC per 1 g TOC
Wt. $H_{Non\text{-}Py}$ (mg/1 g TOC)—Wt. of Hydrogen in Non-Pyrolyzable OM per 1 g TOC
Wt. $C_{HCPy}$ (mg/1 g TOC)—Weight of Carbon in Pyrolyzable HC per 1 g TOC
Wt. $C_{Non\text{-}Py}$ (mg/1 g TOC)—Weight of Carbon in Non-Pyrolyzable OM per 1 g of TOC
% N, S, $O_{OM\ (From\ CHNOS)}$—Percent of elemental Nitrogen, Sulfur, and Oxygen in OM
Wt. $NSO_{OM}$ (mg)—Weight of elemental Nitrogen, Sulfur, and Oxygen in OM
Wt. OM (mg/1 g TOC)—Weight of Total Organic Matter per 1 g TOC
$OM/HC_{Py}$—Ratio of Organic Matter to Analyzed Hydrocarbons by Pyrolysis engineer can efficiently and effectively utilize these data to make judgments regarding the effect of the tar at any depth in this well.

Dynamic testing data for the well can also be used to determine how much tar or pyrobitumen relative to porosity causes a detrimental impact on reservoir performance. In any case, the ability to provide geochemical data in quantitative units in accordance with the invention that can be easily related to reservoir performance by non-geochemists is an important advancement that has not been provided by other geochemical analytic methods used to assist in reservoir characterization.

The volume of organic matter (VOM) method as applied to determine the volume of various organic end-members in a sample of oil reservoir rock provides a much needed complement to currently available petrophysical methods that are employed to assess tar occurrence. Known methods for quantifying organic matter components through physical separations are time-consuming and are subject to a variety of difficulties in separating organic material from rock and ultimately obtaining accurate data so that the components can be mass-balanced. Purely analytical methods to assess the quantities of these materials require that each sample be subjected to a series of sophisticated tests, which are both costly and highly time-consuming.

The method of the invention provides highly reproducible results that can be applied quickly and inexpensively to a large number of samples and provides other advantages that outweigh the under-reporting of hydrocarbon structures found in non-hydrocarbons. Moreover, the amount of under-reporting can be reasonably estimated for various organic matter types through the application of elemental analysis and total organic carbon analysis to a relatively few representative samples. Due to the fact that hydrogen comprises a relatively small portion of the weight of the organic matter and that the total quantity of carbon can be determined very accurately via total organic carbon analysis, the error associated with applying such corrections is small and estimated to be no more than about 1.5%.

The volume of organic matter method of the present invention thus provides a much needed complement to petrophysical methods that are currently employed to assess tar occurrence in oil reservoir characterization. As previously noted, the assessment of tar and/or pyrobitumen in a reservoir has been complicated by the fact that such material does not occur as a uniform composition in reservoirs. Instead, reservoirs typically contain mixtures of various materials such as oil, tar and pyrobitumen, which spatially exhibit ever-changing amounts of each component. The present invention obviates the prior art methods of quantifying these components through physical separations that are time-consuming, costly and subject to a variety of difficulties associated with separating organic material from rock and ultimately obtaining accurate data where the components can be mass-balanced.

The preferred embodiments of the invention have been described and it will be apparent to those of ordinary skill in the art from this description that various modifications and substitutions can be made, so that the scope of the invention is to be determined by the claims that follow.

We claim:

1. A geochemical analysis method for determining the volume of individual organic matter (OM) components having known properties that are present in a sample of oil reservoir rock taken from a specific oil field, where the individual organic matter components correspond to end-member components (x) selected from the group that includes oil, tar, pyrobitumen, kerogen, coal, diesel and drilling mud, the method comprising:

a. analyzing pyrolysis data for a plurality of samples of oil reservoir rock for the presence of one or more end-member components in each sample;
b. selecting rock samples having a nearly uniform composition of a specific end-member;
c. separating any moveable hydrocarbon components from each of the selected rock samples by extraction with cyclohexane, retaining both the solvent extract and the extracted rock sample;
d. separating any soluble tar from the extracted rock by further extraction with methylene chloride, retaining both the tar extract and the extracted rock sample;
e. separating any residual organic matter from the polar solvent-extracted rock by a demineralization process;
f. analyzing all solvent extracts and the residual organic matter from the demineralization process by elemental analysis to determine the weight percentages of C, H, N, O, and S in each sample;
g. analyzing all extracts, separated organic matter and extracted rock samples by pyrolysis-TOC analysis to calculate and record the Total Hydrocarbon Index (THI) in mg of hydrocarbon per gram of carbon, as follows:

$$\text{THI} = [(LV + TD + TC)/TOC] \times 100 \quad (3)$$

where:
LV is the weight in milligrams of "light volatile" components of HC released per gram of rock at the static temperature condition of 180° C. for 3 minutes when the crucible containing the rock sample is inserted into the pyrolytic chamber prior to the temperature-programmed pyrolysis of the sample;
HC means compounds, or portions of compounds that have hydrocarbon units with the formula $C_nH_{xn}$, where n is the number of carbon atoms, and x is the average number of hydrogen atoms per carbon atom;
TD is the weight in milligrams of "thermally distillable" components of HC released per gram of rock at a temperature between 180° C. and $T_{min}$(° C.); $T_{min}$(° C.) is the temperature at which HC volatilization is at a minimum between the temperature of maximum HC volatilization for TD and TC, and is determined as $\Delta(HC)/\Delta(T) = 0$;
TC is the weight in milligrams of "thermally crackable" components of HC released per gram of rock at a temperature between $T_{min}$(° C.) and 600° C.; and
TOC is the Total Organic Carbon in terms of the weight percent of organic carbon found in a rock sample;
h. calculating and recording the average amount of hydrogen present in the pyrolyzable and non-pyrolyzable portions of the end-members in accordance with the following:

$$\text{Wt. } H_{HCPy}(\text{mg}/1 \text{ g TOC}) = \% \text{ H } C_nH_{2n}/100 \times \text{THI}(\text{mg HC/g TOC}) \times 1 \text{ g TOC} \quad (5)$$

where:
Wt. $H_{HCPy}$ (mg/1 g TOC) is the weight of Hydrogen in Pyrolyzable HC per 1 g of TOC,
% H $C_nH_{2n}$ is the Wt. percent of Hydrogen in Alkane Structural Units, and $$\text{Wt. } H_{Non-Py} (\text{mg}/1 \text{ g TOC}) = \text{Wt. } H_{OM} (\text{mg}/1 \text{ g TOC}) - \text{Wt. } H_{HCPy} (\text{mg}/1 \text{ g TOC}) \quad (6)$$

where:
% $HC_nH_{zn}$ is 14.3%,
Wt. $H_{Non-Py}$ (mg/1 g TOC) is the Wt. of Hydrogen in Non-Pyrolyzable OM per 1 g of TOC, and $$\text{Wt } H_{OM} (\text{mg}/1 \text{ gm TOC}) = H/C_{OM} \times (1000 \text{ mg C/Mol-Wt}_{Carbon}) \quad (4)$$

where:

H/C$_{OM}$ is Atomic H/C Ratio in Organic Matter;

i. calculating and recording the weight of carbon in the pyrolyzable OM and non-pyrolyzable OM in accordance with the following:

Wt. C$_{HCPy}$ (mg/1 gTOC)=THI(mg/1 gTOC)×1 g TOC−Wt. H$_{HCPy}$ (mg/1 gTOC)  (7)

where:

Wt. C$_{HCPy}$ (mg/1 gTOC) is the weight of Carbon in Pyrolyzable HC per 1 g of TOC, and Wt. C$_{Non-Py}$ (mg/1 gTOC)=1000 mg TOC−Wt. C$_{HCPy}$ (mg/1 gTOC)  (8)

where:

Wt. C$_{Non-Py}$ (mg/1 gTOC) is the weight of Carbon in Non-Pyrolyzable OM per 1 g of TOC;

j. calculating and recording the weight of N, S, O in the organic end-member in accordance with the following:

$$\text{Wt. } NSO_{OM\_} = \frac{(\% \, NSO_{OM}/100) \times \begin{pmatrix} \text{Wt. } C_{HCPy} + \text{Wt. } C_{Non-Py} + \\ \text{Wt. } H_{HCPy} + \text{Wt. } H_{Non-Py} \end{pmatrix}}{(1 - (\% \, NSO_{OM}/100))}; \quad (9)$$

k. calculating and recording the weight of organic matter for each end-member relative to one gram of TOC as follows:

Wt. H$_{HCPy}$+Wt. H$_{Non-Py}$+Wt. C$_{HCPy}$+Wt. C$_{Non-Py}$+Wt.NSO$_{OM}$;  (10)

l. calculating and recording the ratio of organic matter to pyrolizable hydrocarbons (OM/HC$_{py}$) in accordance with the following:

OM/HC$_{Py}$=Wt. OM/THI, or  (11)

OM/HC$_{Py}$=Wt. OM/(Wt. H$_{HCPy}$+Wt. C$_{HCPy}$);  (12)

m. calculating and recording the weight of each selected end-member (X) in milligrams per gram of rock in accordance with the following:

Wt. HC$_{End-Member(X)}$=THC$_{(X)}$×% CoMod Yield$_{End-Member(X)}$  (13)

and

Wt. OM$_{End-Member(X)}$=OM/HC$_{Py}$×Wt. HC$_{End-Member(X)}$;  (14)

n. determining the volume of each selected end-member (X) by dividing the mass of each end-member by the density of the end-member in accordance with the following:

Volume OM$_{End-Member(X)}$=Wt. OM$_{End-Member(X)}$/Density$_{OM}$; and  (16)

o. recording the results of step (n) for each of the end-members and visually displaying the data for analysis.

2. The analytical method of claim 1 which further comprises determining the volume of organic matter end-members as a percentage of total rock volume as follows:

p. providing the values for at least average porosity and matrix density for the reservoir rock at the depth from which the sample was recovered;

q. calculating the bulk volume in microliters in accordance with the following:

Bulk Volume(μl)=1/(matrix density−(matrix density×Φ/100))×1000  (18)

where Φ is the average measured porosity of a rock sample or that assessed by electric logs at a given depth;

r. applying the value of the bulk volume determination of step (q) to the volume of organic matter calculated in step (n) to calculate the volume of the selected organic end-members as a percentage of the reservoir rock sample.

3. The method of claim 2 in which the mass and volume data are recorded and displayed for interpretation by personnel in real time and the interpretative information is used for the geosteering of horizontal well drilling.

4. The method of claim 1 which comprises repeating steps (g) and (n) for a plurality of samples recovered from different depths in a well bore.

5. The method of claim 4 which includes producing a graphic display in the form of a plot of the calculated volume of organic material for at least oil, tar and pyrobitumen versus depth.

6. The method of claim 5 which includes a plot of porosity versus depth on the graphic display.

7. The analytical method of claim 1 in which five end-members are selected.

8. The analytical method of claim 1 in which the selected end-members are oil, tar and pyrobitumen.

9. The method of claim 1 where the density value for oil applied in step (n) is derived from the API Gravity in grams/cm$^3$.

10. The method of claim 1 where the density values for end-members other than oil are determined by analysis of representative end-member samples previously obtained from the oil field.

11. The method of claim 1 in which compositional modeling data is employed that is based on a solution that sums the difference between the calculated yield and the actual yield over a plurality of data steps for each sample of organic matter end-member selected to iteratively minimize aggregate error among all of the selected end-members.

12. The method of claim 1 in which the elemental analysis is performed on representative portions of reservoir rock core samples previously taken from the oil field.

13. A method for determining the volume of organic matter (VOM) in each of a plurality of end-members present in oil reservoir rock through which a well passes, wherein the end-members are consistent types of organic matter and/or hydrocarbons that can be distinguished through pyrolytic analysis, the end members being selected from the group consisting of oil, soluble tar, pyrobitumen, kerogen, coal, diesel, drilling mud contaminants, and other locally significant components, the method comprising:

a. collecting and preparing rock samples for anlaysis by the Pyrolytic Oil-Productivity Index (POPI) and the Apparent Water Saturation (ASW) Method, ("POPI/AS$_w$ method");

b. completing the analysis to obtain raw data for each sample that includes, comma separated values (CSV) files consisting of time step, temperature, and FID response or HC yield;

c. identifying the appropriate local organic matter end-members present in the reservoir rock to employ in compositional modeling from the group that includes oil, tar, pyrobitumen, coal, kerogen, diesel, and drilling mud contaminants;

d. obtaining physical and chemical properties of the selected organic matter end-members, the properties including THI, atomic H/C ratio, hydrocarbon density, and weight percentages of C, H, N, O, and S from elemental analysis, and calculate and record the ratio of organic matter to pyrolizable hydrocarbon yield from the end member ($OM/HC_{Py}$);

e. calculating and recording the relationship between the pyrolytic yield and mass/volume for each selected end-member;

f. analyzing routine samples from the well and performing compositional modeling with end-members that have been identified for the reservoir;

g. completing the compositional modeling to determine the relative hydrocarbon yields in mg of HC/g of rock for each organic end-member sample analyzed;

h. determining the mass and volume for each selected end-member in all samples and assessing reservoir impairment;

i. using available matrix density, grain density and porosity values for the portion of the reservoir rock through which the well passes, calculating and recording the volume percentages of each selected end-member in all of the samples analyzed; and j. preparing graphic plots of the volume of end-members found in each sample as a function of depth and visually displaying the data for interpretation.

14. The method of claim 13 which includes graphically plotting the volume of immovable hydrocarbon end-members in relation to the reservoir porosity to identify any portions of the reservoir through which the well passes on which said immovable hydrocarbons will have a detrimental effect on hydrocarbon flow.

* * * * *